United States Patent [19]

English et al.

[11] Patent Number: 4,538,545

[45] Date of Patent: Sep. 3, 1985

[54] FOAM GENERATING AND DISTRIBUTING MANIFOLD APPARATUS

[75] Inventors: Donald C. English; Bruce W. Hicks, both of Rio Linda, Calif.

[73] Assignee: Rio Linda Chemical Co., Inc., Sacramento, Calif.

[21] Appl. No.: 629,778

[22] Filed: Jul. 11, 1984

[51] Int. Cl.³ .............................................. B05C 5/00
[52] U.S. Cl. .................................... 118/679; 118/668; 118/612; 118/324; 422/133; 252/359 E; 261/DIG. 26
[58] Field of Search .................... 422/133; 252/359 E; 261/DIG. 26; 239/398, 407, 343, 342; 264/50; 118/668, 679, 324, 612

[56] References Cited

U.S. PATENT DOCUMENTS 2,680,010 6/1954 Dubay .............................. 239/343 X
3,744,775 7/1973 Greenberg .................. 261/DIG. 26
4,070,302 1/1978 Chatterton ...................... 252/359 E
4,394,289 7/1983 Brown et al. ................ 261/DIG. 26

OTHER PUBLICATIONS

Patentanmeldung, Klasse 2b Gruppe 202, G12064 III/2b, 12/8/1955.

Primary Examiner—Shrive P. Beck
Attorney, Agent, or Firm—Leonard Bloom

[57] ABSTRACT

A foam generating and distributing manifold device for generating and transporting foam cleansing and sanitizing agents having a manifold chamber with a centrally disposing frothing tube to generate foam which migrates upwardly within the chamber to a plurality of annularly disposed egress ports through which foam is distributed to a series of substantially equidistant supply conduits thereafter migrating to a distribution manifold which distributes the foam evenly upon, for example, conveyor belts used in food processing or the like.

14 Claims, 4 Drawing Figures

FOAM GENERATING AND DISTRIBUTING MANIFOLD APPARATUS

BACKGROUND OF THE INVENTION

The instant invention relates generally to continuous foam generating devices, and more specifically to a distribution manifold for foam cleaning or sanitizing to evenly generate and distribute foam at multiple points of use.

It is well known in the prior art to employ foam cleansing and/or sanitizing agents as an effective way to maintain clean, sanitary equipment surfaces in, for example, the food processing, paper, and pharmaceutical industries. Employing foam allows for a thorough yet cost-effective dispersion of the cleansing agents over the surfaces of the equipment to be cleaned. Using foam instead of liquid streams to sanitize and cleanse effectively reduces the waste produced in over-spraying and greatly alleviates the problem of collecting and disposing of excess fluids used in the sanitizing process. However, chemicals that form foam for cleansing applications such as, cationic, anionic, and nonionic surfactants produce foams that are easily broken down making them difficult to distribute properly. It is necessary that the foam maintain a certain consistency and bubble density in order to effectively coat the surfaces of the equipment which is being treated. If the foam becomes too runny or too dry, it will not completely cover or properly cling to the equipment surfaces, therefore not providing adequate cleansing and/or sanitizing of same.

Employing an automatic foam system produces a number of benefits, not the least of which is the reduced need for personnel to distribute and apply cleansing agents to strategic equipment. As well as reducing labor costs, an automatic foam generation and distribution system prevents personnel from possibly being exposed to dangerous chemicals, namely fungicides, bacteriacides, and other caustic agents. Although the benefits are numerous, the major technical problem has been in the transportation of a cleaning foam for multiple distribution, which foam maintains a good quality in the sense of density and content. Therefore, there exists a strong felt yet unfulfilled need for the device according to the instant application which provides a manifold distribution network and foam generating chamber which evenly distributes a consistent, effective foam to multiple distribution points.

The following list of citations represent prior art devices of which applicant is aware that may be germane to the patent process:

| U.S. Pat. No. | Inventor | Issue Date |
| --- | --- | --- |
| 3,823,727 | Fry | July 16, 1974 |
| 4,134,741 | Elsberad, et al. | Jan. 16, 1979 |
| 4,394,289 | Brown, et al. | July 19, 1983 |

The patent to Elsberad, et al., U.S. Pat. No. 4,134,741, is of interest since the device disclosed addresses the problem of distributing foam over equipment surfaces, more specifically, electronic precipitators. It should be noted that a primary problem pointed out in the above cited patent involves the handling and distribution of cleaning foams, the solution to which involves, in this instance, a complex array of 90° elbow connections and T-connectors to make up a manifold to distribute a high quality foam which is not overly deteriorated in transportation. It can be seen in FIGS. 2, 3, 4, 5 and 6 of the instant citation that attempts at multiple point distribution networks have relied upon dividing a single foam outlet conduit 42 into multiple conduits 29a, b, c and d, to distribute the foam therethrough. Applicant's observations and experiments have revealed that attempts at dividing a single foam outlet conduit into more than two subdivided conduits results in foam deterioration and decomposition to such an extent that the quality of the foam eventually emanating from the distribution nozzles or ports is of inadequate quality to accomplish the desired results of properly cleansing equipment surfaces. Furthermore, the distribution network suggested by the instant citation creates an expensive and awkward plumbing network which is essentially eliminated by the device according to the instant application.

In certain technological applications such as those required by the pharmaceutical, biotechnology, paper and food processing industries, an automatic foam sanitizing system may include upwards of 900 individual foam discharge ports. By way of example, in the fruit canning industry, very sophisticated pitters are used to remove seeds from fruit, and a typical automatic foam cleansing apparatus applied to such equipment will require as many as several hundred individual foam discharge points. If a single foam generating device is used to supply the hundreds of individual discharge ports, then a massive plumbing network is required to connect the numerous ports to the source of the foam. In this instance, the quality of the foam deteriorates so radically that it renders this type of system inoperative. Employing applicant's invention, numerous manifold foam generating and distribution chambers are deployed at strategic positions throughout the processing plant so that the foaming agents are frothed into a foam form at a situs proximate to the equipment to be sanitized. This provides the advantage of limiting the asportation requirements of the foam thereby maintaining a high quality and consistency for effective sanitizing. Furthermore, the device according to the instant application provides numerous flexible conduit means to carry the foaming agent in an undisturbed path from the foam generating chamber to the distribution port. No one flexible conduit is divided more than twice, thereby virtually eliminating the problems associated with multiple divisions of an egress conduit.

The remaining citations further delineate the state of the art. However, none of the citations taken singly nor in any conceivable combination would appear to anticipate nor render obvious that which is disclosed herein.

SUMMARY AND OBJECTS OF THE INVENTION

The foam generating and distribution manifold according to the instant application overcomes prior art deficiencies by providing a simple, relatively uncomplicated mixing and generating manifold chamber which can be deployed at multiple stations throughout, for example, a processing plant so that foam can be generated in proximity to the apparatus to which it is applied, thereby eliminating the problems associated with transporting generated foam through conduits for any great distance. Furthermore, the instant manifold distribution device is provided with a plurality of flexible egress conduits which transport the foam to multiple distribution ports in a consistent fashion, thereby supplying a high quality consistent density foam which evenly coats the surfaces to which it is applied. This is accomplished by providing each port with a flexible conduit that is in direct fluid communication with the manifold generating chamber, this communication being separate from the conduits supplying any other distribution port. Thus each port has its own integral supply line, or at most each distribution port shares a supply line with only one other distribution port. Furthermore, experimentation has revealed that in order to supply a good quality and consistent foam product at each distribution port, conduit supply lines must be substantially the same length and diameter, otherwise the foam quality and density varies from port to port. In addition, the placement of the egress ports on the generating manifold chamber in relation to the interior foam generation tube is a critical factor in determining the quality of the foam generated and transported through the egress ports into the supply conduits. A configuration such as that provided by the instant invention ensures that foam of a consistent quality and density is furnished to the supply conduits which are all essentially coplanar in relation to the manifold generating chamber.

Accordingly, it is the primary object of the present invention to provide a novel foam generating and distributing manifold network that can supply a consistent and high quality foam to both the top and bottom surfaces, for example, of a conveyor belt apparatus.

It is a further object of the present invention to provide a unique foam generating and distributing manifold which provides a foam of consistent quality and density, thereby eliminating the problems of runny or dry foam which are caused by the foam transportation methods of prior art devices. This is accomplished by providing a foam distribution network with multiple stations, each station having a foam generating and distributing manifold according to the instant disclosure. Thus the foam is generated in proximity to the surfaces to which it is applied, thereby greatly reducing the problems of foam deterioration.

It is yet another object of the present invention to provide a novel foam generating and distributin manifold system which is provided with a foam generating chamber having a series of essentially coplanar egress ports, thereby ensuring a consistent foam quality because the chamber is being tapped at a certain level where the geometric configuration of the foam generated therein is the most consistent.

It is yet another object of the present invention to provide a novel foam generating and distributing manifold system which supplies a foam distribution network that is significantly less dependent on precise hydraulic calculations in order to balance a multiple point delivery system.

It is yet a further object of the present invention to provide a novel foam generating and distributing system which is capable of generating and transporting a foam to a large number of individual discharge points while preserving the foam's desireable characteristics as to firmness, dryness, and even distribution.

It is a still further object of the present invention to provide a novel foam generating and distribution system that operates automatically and can be used in conjunction with a micro processor to foam and rinse desired equipment at preset times. Furthermore, additional capabilities such as sensing and adjusting hydraulic and pneumatic pressures in the supply lines to the manifold chambers can be provided, along with the capability provided by product sensors which could, for example, sense the presence of food products on a conveyor belt system and thereafter halt any foaming operations to prevent the contamination of any food products by the cleansing agents carried by the foam.

It is still another object of the present invention to provide a unique foam generating and distributing system which can clean or sanitize equipment and requires minimal operating personnel in order to monitor and adjust the systems, but is capable of the special cleaning requirements of, for example, food, paper, and pharmaceutical industry requirements.

These and other objects will become manifest when viewed in light of the following detailed descriptions taken in conjunction with the appended drawing figures.

DETAILED DESCRIPTION OF THE PREFERRED EMBODIMENT

Figure 2:
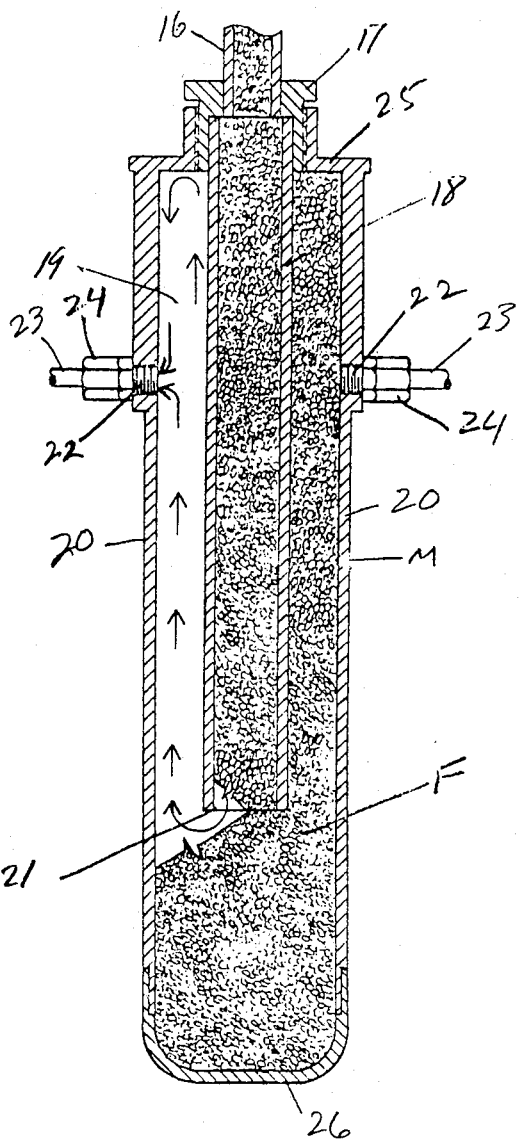
FIG. 2 is a sectional view of that which is shown in FIG. 1 taken along lines II—II.

Referring now to the drawings in detail, wherein like reference numerals represent like parts throughout the various figures, reference numeral 10 refers generally to the foam generating and distributing manifold which is provided with a liquid inlet conduit 11 and a pneumatic inlet conduit 12, the pneumatic inlet conduit being provided with an adjustable regulator and gauge 13 to adjust the pressure of the gas supplied therethrough. Thus a source of pressurized gas, usually air, is provided through conduit 14 regulated by the regulator 13 then joins the liquid supply conduit 11 at the juncture 15, thereafter the liquid and gas begin to mix to form foam in the primary frothing tube 16 which extends through the cap 17 after which the tube 16 increases in cross sectional area to form an extended frothing tube 18, as best shown in FIG. 2. The frothing tube 18 is contained within a chamber 19 having exterior walls 20 which define the interior chamber space 19. The frothing tube 18 extends substantially below the longitudinal midway point M of the chamber 19 providing at a downward end thereof a frothing port 21 where the foam formed from the pressurized gas and liquid introduced therein emanates into the chamber 19.

A series of coplanar foam manifold egress ports 22 are provided substantially above a longitudinal midpoint M of the foaming chamber 19. The foam egress ports are disposed in a coplanar annular fashion about the outer surface of the sidewalls 20 of the chamber 19 and are in fluid communication with the interior chamber 19 so that foam may pass therethrough into the foam supply conduits 23 through the fastening nipples 24. It should be noted that a plurality of foam egress ports may be provided around the chamber walls 20 and in a preferred embodiment, the egress ports are equidistant from one another and substantially coplanar so that no one port is any closer to the midpoint M or the frothing port 21 than any other egress port 22. Thus, the foam that emanates from the frothing port 21 is distributed throughout the chamber 19 and may migrate into the egress ports 22 from various directions as indicated by the arrows in FIG. 2. The placement of the frothing port 21 substantially below the plane of the egress port 22 is a critical factor in ensuring that a consistent density and quality of foam migrates into the supply conduits 23. Because the foam is released into the chamber at a lower level than the level of the ports 22, by the time the foam migrates to the port level the geometric configuration of the bubbles comprising the foam has stabilized so that a consistent desireable quality foam having the correct firmness, moisture content and density is allowed to enter the supply conduits 23 through the ports 22. It should be further noted that the generating and distributing manifold 10 should be fixed in a substantially vertical position in relation to the gravitational field to provide the optimum results.

As the liquid and the pressurized air pass into the chamber 19 through the frothing tube 18, a partially generated foam or mixture of air and foam is discharged into the chamber 19 which acts as a vessel providing a relatively large open space in which a consistently configured foam can be generated. The chamber itself can be of any desired configuration as shape is not seen as critical, as long as the chamber is able to withstand the operating pressures of the system. In a preferred embodiment, the chamber may be formed from an elongated cylindrical pipe with capped ends. By way of example only, the chamber may be formed from a piece of 4" diameter pipe approximately 12" to 20" long and capable of carrying a flow rate of two to three gallons per minute. The frothing tube 18 is centrally disposed through the chamber top 25 and is of substantially less diameter than the chamber itself. The frothing tube 18 extends downwardly within the confines of the chamber 19 past the midpoint M towards the chamber bottom 26 terminating at a frothing port 21 substantially above the chamber bottom 26. Thus the chamber 19 provides a large enough interior space for the final foam F to be formed and properly configured.

The chamber configuration, i.e., width and heighth, is relative to the desired flow rate. Similarly, the number of egress ports 22 that can be accomodated is relative to the desired flow rate and fluid pressures employed. Similarly, egress port diameter 22 and supply conduit diameter 23 are dependent upon flow rates and fluid communication distances. By way of example, port and conduit diameters generally vary from $\frac{1}{8}$" to $\frac{1}{2}$"; however, optimum foam quality can apparently be achieved by employing a $\frac{1}{4}$" diameter egress port 22 and supply conduit 23.

Figure 1:
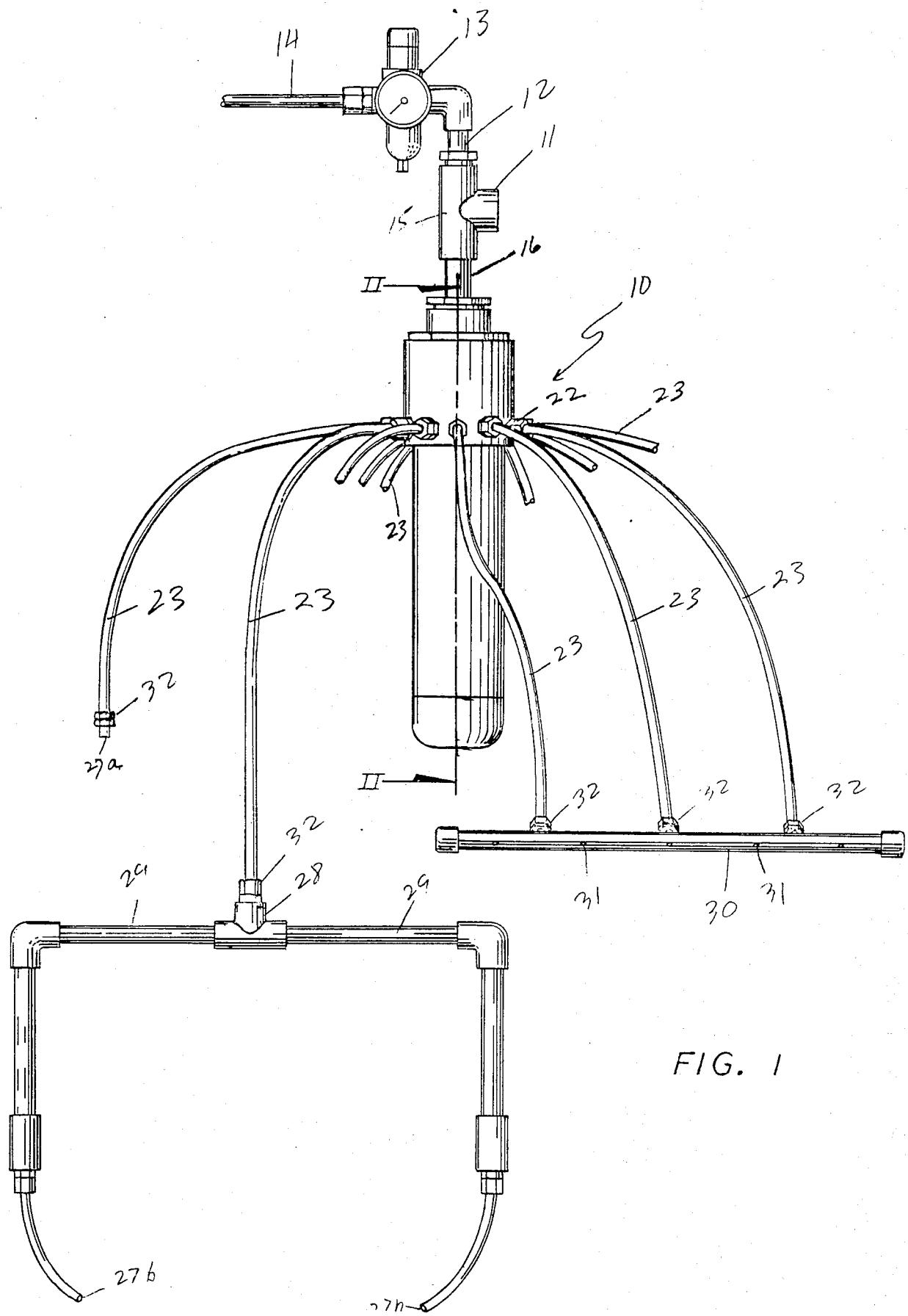
FIG. 1 is a front view of the foam generating and distributing manifold showing the various distribution port configurations including the single port, the double port configuration, and the multiple port/multiply supply conduit configuration.
Figure 4:
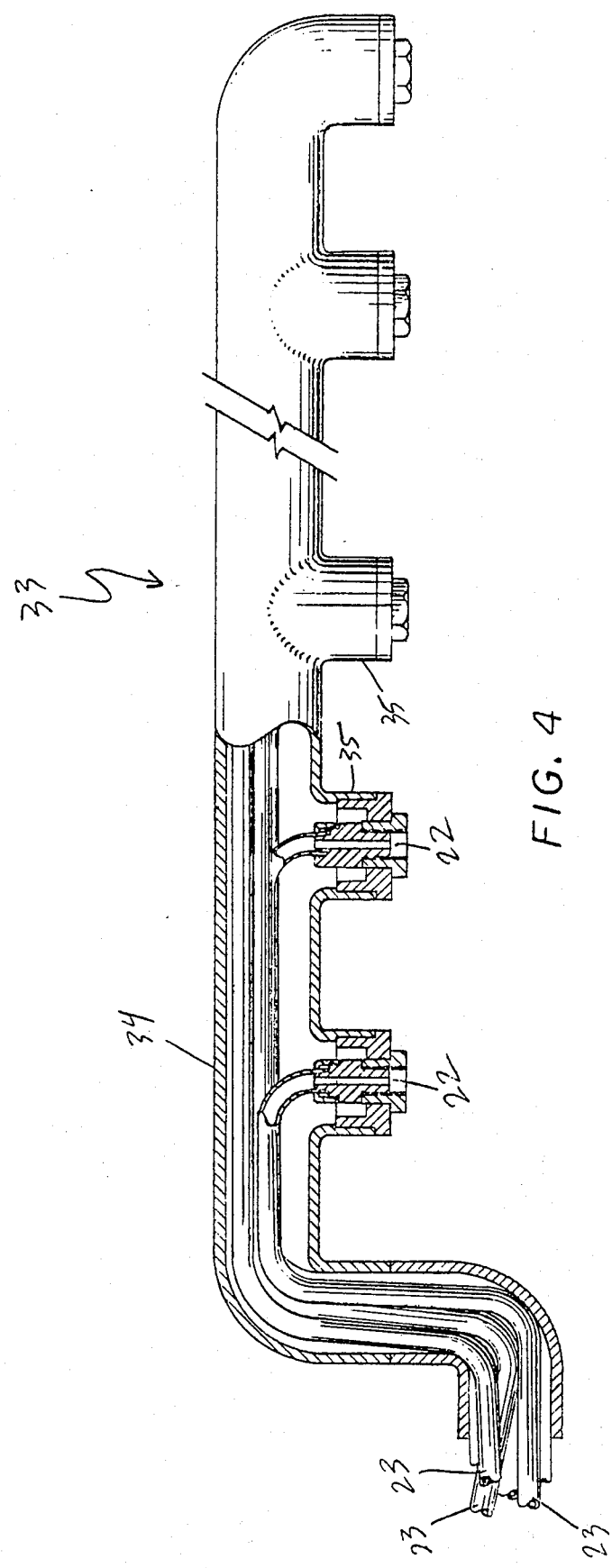
FIG. 4 is a partial sectional view of the distribution port configuration shown in FIG. 3, the flexible conduits each separately supplying an individual distribution port to ensure consistent foam quality.

The supply conduits 23 emanating from the chamber 19 are formed from a flexible conduit material and provide for fluid communication from the chamber 19 to the distribution ports 27. The distribution ports may be variously configured as shown in FIGS. 1 and 4. Referring to FIG. 1, a single supply conduit 23 may be employed with a single distribution port 27a to supply foam F to a particular surface. In another configuration, a single supply conduit 23 can be divided by employing a T section 28 which essentially divides the supply line 23 into two supply pipes 29 which terminate in separate distribution ports 27b. Once again, it should be noted that no single supply conduit 23 should be divided more than once into separate supply pipes 29 or the like because further serial divisions result in inferior foam characteristics.

A further distribution means is shown in FIG. 1 as a distribution bar 30 having a plurality of distribution nozzles 31, said distribution bar 30 being supplied by a series of distribution conduits 23 having on ends thereof distribution ports 22 which are fixed by means of a fastening nipple 32. It should be noted that the number of nozzles 31 in a bar 30 never exceeds two times the number of supply conduits 23 which supply foam to the distribution bar 30. This keeps within the general axiom that no one supply conduit 23 should be divided into more than two ultimate dispensing nozzles.

Referring now to FIG. 4, a distribution manifold, generally referred to by reference numeral 33, is shown in which a plurality of distribution ports 22 are contained therewithin. The distribution manifold 33 consists of an outer housing 34 which provides a protective shroud to encase a series of supply conduits 23 each separate and integral from one another and each supplying a separate distribution port 22 affixed in coplanar series within similar protuberances 35 which capture and align the distribution ports 22 so that the foam emanating therefrom is directed downwardly to provide an even distribution pattern across any surface to which the distribution manifold is directed. Any number of distribution ports 22 can be accomodated within a distribution manifold 33 according to the particular requirements of the environment.

It should be noted with particularity that in a most preferred embodiment, each distribution port 22 is supplied by a separate supply conduit 23 and that the quality of the foam that emanates therefrom is somewhat dependant upon the fact that each supply conduit 23 is of substantially the same length so that the foam travelling therethrough encounters similar transportation frictions and pressures no matter which of the various supply conduits 23 it travels through. Thus, every distribution port 22 supplies a foam of substantially similar characteristics, therefore adjusting the foam quality and density can be done by a single adjustment of the pneumatic pressure or the liquid pressure supplied to the generating manifold 10 instead of having to attempt to adjust various conduits.

Figure 3:
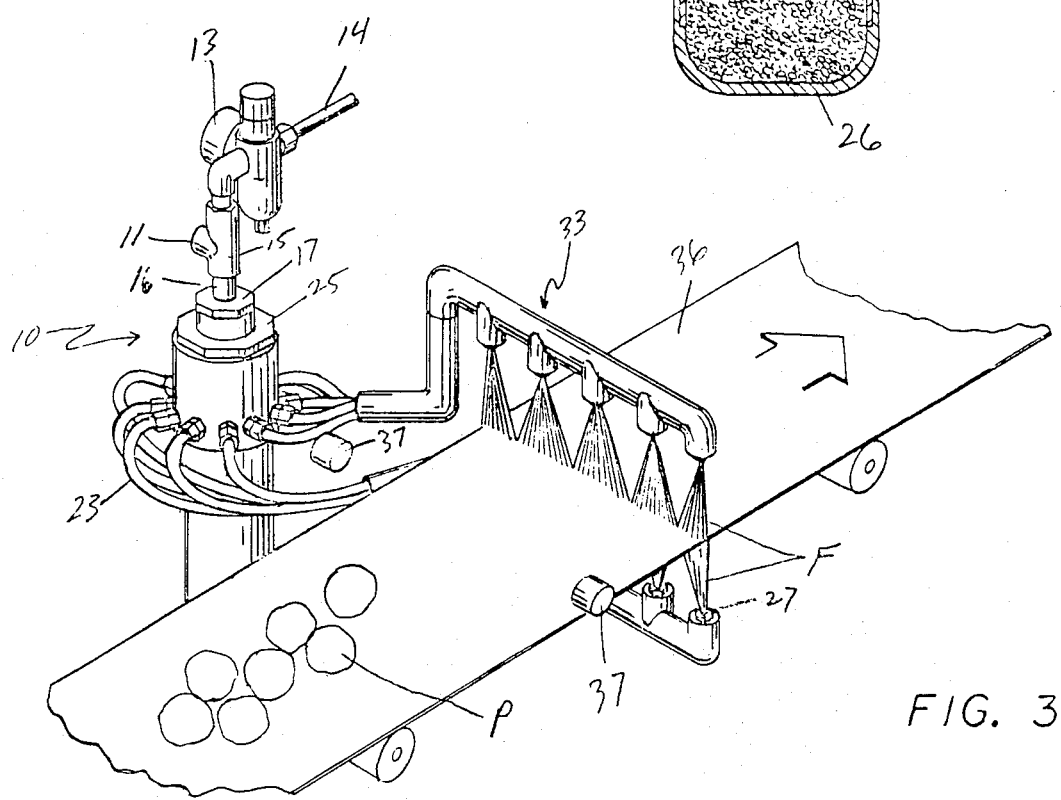
FIG. 3 is a perspective view of the foam generating and distributin manifold as it would be applied to a conveyor belt in a food processing environment with a particular distribution port configuration such that both the top and bottom surfaces of the conveyor belt could be cleansed with the foaming agent. In addition, sensors are indicated which detect the presence of food product on the belt, thereby halting the foaming activities.

By way of example, in use and operation, the manifold system disclosed herein may be applied to a conveyor belt in a food processing environment as depicted in FIG. 3, in which the conveyor belt 36 is travelling in the direction of the arrow thereupon and passes beneath and above a series of two distribution manifolds 33 supplying a constant automatic distribution of foam F. The foam may carry a bacteriacide so that a sanitation process is constantly being accomplished when product is not being processed thereupon. When there is product P upon the belt, then as it passes by the two product sensors 37, which may be of any commercially available type such as photometric, a signal is processed and a command is generated which immediately stops the foaming activity so that the chemicals contained within the foam do not contaminate the product P.

It should be noted that numerous structural changes and modifications may be resorted to without departing from the spirit of the invention. For example, it is contemplated that the system may also include the use of a microprocessor in combination with a controller encompassing various selanoid switches so that foam and rinse cycles can be easily controlled.

What is claimed is:

1. A foam generating and distribution apparatus, comprising:
    a foam generating chamber defined by top, bottom and side walls,
    ingress means provided in said top wall of said chamber to receive therethrough pressurized gas and a liquid,
    a frothing conduit surrounding said ingress means and extending downwardly therefrom into said chamber to conduct and mix said gas and said liquid to generate foam,
    egress ports in fluid communication with said chamber annularly disposed through said side walls substantially above the lower termination point of said frothing conduit, and
    supply conduits in fluid communication with said egress ports having on an opposed end distribution ports to distribute said foam.

2. The device as recited in claim 1, wherein said foam generating chamber further comprises a substantially cylindrical elongated chamber having a closed bottom wall and a top cap which defines said ingress means, said chamber providing a relatively large interior space in which partially generated foam is partially pressurized and becomes of substantially uniform density and bubble configuration.

3. The device as recited in claim 1, wherein said ingress means provided in said cap of said chamber further comprises a regulated source of pressurized gas in fluid communication with a regulated source of a liquid foaming agent, said liquid and said gas being simultaneously introduced into said frothing conduit which surrounds said ingress means in the interior of said chamber.

4. The device as recited in claim 1, wherein said frothing conduit further comprises an elongated tubular conduit of substantially less diameter than the diameter of said chamber, said conduit on one end surrounding said ingress means and extending downwardly therefrom and terminating in a frothing port, said port being centrally disposed within said chamber at a point substantially below the longitudinal midpoint of said chamber, so that the gas and the liquid are partially frothed into a foam within said frothing conduit and propelled outwardly from said frothing port into the confines of said chamber after which said foam migrates upwardly within said chamber under a certain pressure so that said foam becomes substantially consistent as to density and bubble configuration.

5. The device as recited in claim 4, wherein said frothing conduit is centrally disposed within said chamber and extends downwardly within the confines of said chamber substantially two-thirds to three-fourths of the longitudinal length of said chamber.

6. The device as recited in claim 1, wherein said egress ports further comprise a plurality of annularly disposed ports equidistant from one another and all substantially coplanar horizontally so that no one said port is disposed closer to said frothing port of said frothing conduit than any other said egress port.

7. The device as recited in claim 6, wherein said egress ports are disposed above the longitudinal midpoint of said chamber.

8. The device as recited in claim 1, wherein said supply conduits further comprise substantially equal length flexible conduits in fluid communication with said egress ports and terminating in said distribution ports from which foam emanates to be distributed upon various desired surfaces.

9. The device as recited in claim 1, wherein said flexible supply conduits are gathered into a distribution manifold which encases various said supply conduits and fixes said distribution ports in such a manner so that foam emanating therefrom is targeted in a desired dispersion pattern so as to disseminate foam over various contoured surfaces in any desired density.

10. The device as recited in claim 1, wherein said supply conduits further comprise a division of any single said supply conduit into two further supply conduits terminating in no more than two said distribution ports.

11. The device as recited in claim 1, wherein said supply conduits are flexible tubular conduits of substantially $\frac{1}{4}''$ diameter.

12. The device as recited in claim 1, wherein a series of said distribution ports at the ends of said supply conduits are affixed in fluid communication with a distribution bar having a series of distribution nozzles, said bar being hollow and having closed ends and said nozzles never exceeding two times the number of said supply conduits affixed thereto.

13. The device as recited in claim 1, wherein said distribution ports are collected into said distribution manifold and applied to the top and bottom surfaces of a conveyor belt in conjunction with product sensors disposed alongside said conveyor belt so that when a product is detected upon the top surface of said conveyor belt, the foaming process is immediately halted to prevent contamination of the product on the belt by the foaming agent.

14. A foam generating a distributing apparatus, comprising:
    a foam generating chamber defined by top, bottom and side walls,
    ingress means provided in said top wall of said chamber to receive therethrough pressurized gas and a liquid,
    a frothing conduit surrounding said ingress means and extending downwardly therefrom into said chamber past the longitudinal midpoint of said chamber to conduct and mix said gas and said liquid to generate foam,
    a plurality of egress ports in fluid communication with said chamber annularly disposed through said side walls substantially above the longitudinal midpoint of said frothing conduit, and
    a plurality of substantially equal length supply conduits in fluid communication with said egress ports, said conduits having on opposed ends thereof distribution ports to distribute said foam.

* * * * *